United States Patent
Fuhr et al.

(10) Patent No.: US 6,646,238 B1
(45) Date of Patent: Nov. 11, 2003

(54) METHOD AND DEVICE FOR A ACCOMODATING SAMPLES ON CRYOSUBSTRATES

(75) Inventors: Günter Fuhr, Berlin (DE); Rolf Hagedorn, Berlin (DE)

(73) Assignee: Evotec Oai AG, Hamburg (DE)

( * ) Notice: Subject to any disclaimer, the term of this patent is extended or adjusted under 35 U.S.C. 154(b) by 0 days.

(21) Appl. No.: 10/009,911

(22) PCT Filed: May 5, 2000

(86) PCT No.: PCT/EP00/04063

§ 371 (c)(1),
(2), (4) Date: Mar. 19, 2002

(87) PCT Pub. No.: WO00/68663

PCT Pub. Date: Nov. 16, 2000

(30) Foreign Application Priority Data

May 7, 1999 (DE) .......................... 199 21 236

(51) Int. Cl.⁷ .................................. H05B 3/06
(52) U.S. Cl. .................. 219/521; 435/1.3; 435/284.1; 435/285.2; 62/63; 62/65
(58) Field of Search .................. 219/521, 525, 219/524, 537, 539, 535; 435/1.3, 405, 40.51, 284.1, 186.2, 286.4, 287.1, 287.3, 288.7, 288.4, 288.6, 288.3, 288.2; 62/63, 65, 78

(56) References Cited

U.S. PATENT DOCUMENTS

| 5,050,470 A | 9/1991 | Ward |
| 5,233,844 A | 8/1993 | Knippscheer et al. |
| 5,925,511 A | 7/1999 | Fuhr et al. |
| 5,998,129 A | 12/1999 | Schütze et al. |

FOREIGN PATENT DOCUMENTS

| AT | 318 253 | 10/1974 |
| DE | 20 28 898 B2 | 12/1971 |
| DE | 197 16 913 | 11/1998 |
| DE | 197 16 913 A1 | 11/1998 |
| EP | 0 103 477 B1 | 3/1984 |
| EP | 0 475 409 B1 | 3/1992 |
| EP | 0 084 073 | 11/1997 |
| EP | 0 804 073 B1 | 11/1997 |
| WO | WO 94/18218 A1 | 8/1994 |
| WO | WO 97/29354 A1 | 8/1997 |
| WO | WO 98/43592 | 10/1998 |
| WO | WO 98/43592 A2 | 10/1998 |

OTHER PUBLICATIONS

Franks, F. "Biophysics and Biochemistry of Low Temperature Freezing" in *Effects of Low Temperatures on Biological Membranes*, editor G. J. Morris et al., 1981.

Liebo, S. P. et al., *Crybiol.*, vol. 8, pp. 447–452, 1971.

Mazur, P., "Stopping Biological Time; The Freezing of Living Cells" in *Ann. N.Y. Acad. Sci.*, vol. 541, pp. 514–531, 1988.

Ohno, T. "A Simple Method for in situ Freezing of the Anchorage–Dependent Cells Including Rat Liver Parenchymal Cells" in *Cytotechnology*, 5: 273–277, 1991.

Plattner, S. H. et al., "Cryofixation of Single Cells by Spray–Freezing" in *Freeze–Etching Techniques and Application*, Chapter 8, pp. 81–100, 1973.

Robinson, D. G. "Präparationsmethodik in der Elektronenmikroskopie", 1985.

*Primary Examiner*—Teresa Wallberg
*Assistant Examiner*—Shawntina Fuqua
(74) *Attorney, Agent, or Firm*—Caesar, Rivise, Bernstein, Cohen & Pokotilow, Ltd.

(57) ABSTRACT

For sample picking on a cryosubstrate, on which multiple cryopreserved samples are each positioned at preselected sample positions, individual samples are selectively separated mechanically or thermally from the cryosubstrate and transferred to a target substrate.

28 Claims, 9 Drawing Sheets

METHOD AND DEVICE FOR A ACCOMODATING SAMPLES ON CRYOSUBSTRATES

BACKGROUND OF THE INVENTION

The invention concerns a method for sample picking on cryosubstrates, particularly a method for transferring samples in a cryopreserved or thawed condition from a cryosubstrate to a target substrate. The invention also concerns a device for implementing a method of this type and a cryosubstrate which is functionally textured for sample taking.

The operation of cryobanks for preserving biological cell material is generally known in cell biology, molecular biology, and genetic engineering. In a cryobank, the cell material is kept available for decades, with, for example, suspended cells being frozen in small-volume containers (volumes range from 0.1 ml to a few ml) filled with a cryoliquid. In order to ensure the viability of the cell material after thawing, numerous procedures have been developed which, for example, relate to the timing of the thawing, media additives, container shapes, and similar things. With conventional cryobanks, survival rates ranging from a few percent up to 90% are achieved during thawing. Although this is already a relatively good result and cryobanks have found worldwide distribution, the following disadvantages are connected with the cryopreservation procedures disseminated until now.

The position of individual cell material samples in the volume of the cryoliquid is unknown during both the freezing and the thawing procedures. The material samples are not accessible in the preserved, deep frozen state. However, there is interest in, for example, removing single cells from cryopreserved material, measuring, or changing them. However, in order to be able to remove cells, the entire sample must be thawed. This requires costly recultivation of the cell material to compensate for the thawing losses. Over the course of time, the cryopreserved material thus no longer contains only the originally preserved cells, but a mixture of daughter cells of greatly varying generations, which restricts the specificity and reproducibility of cell investigations. In order to subject all material samples in a cryocontainer to the same cooling progression, extremely slow freezing procedures must be provided, since the cooling proceeds from the container walls and all samples in the cryovolume are to experience approximately the same temperature progression over time. Finally, the suspension medium (cryoliquid) prevents or makes more difficult measurement and processing of single cells at low temperatures.

There is an interest in new cryopreservation technologies for overcoming the disadvantages mentioned and for opening new fields for cell preservation, particularly since researches in biotechnology, genetic engineering, and medicine are increasingly directed toward single cells, such as in hybridoma cell production in connection with tumor treatment, stem cell culture, and embryogenesis. The development of new cryopreservation technologies is based on the following knowledge and considerations.

From a physical and physiological viewpoint, a cell frozen at −196° C. is in a solid state. The metabolic processes have come to a complete standstill down to the molecular level. Cell changes only arise through slow restructuring (e.g. through the growth of ice crystals at temperatures above −80° C.) and through damage due to cosmic radiation. The latter, however, has a rate of approximately 90% damage after 30,000 years, which is non-critical for practical applications. In the deep frozen state, cells should therefore able to be measured, treated, changed, sorted and otherwise manipulated in a mechanically robust way without time pressure and with the highest precision. However, this assumes the ability to individually handle the cells in the cryomedium and the availability of tools for cell manipulation.

The physical and chemical procedures during the freezing or thawing of biological materials are, for example, described in the publication of F. Franks "Biophysics and biochemistry of low temperature and freezing"in "Effects of Low Temperatures on Biological Membranes"(Editor G. J. Morris et al., Academic Press, London, 1981) or P. Mazur in "Ann. N.Y. Acad. Sci.", vol. 541, 1988, p. 514 et seq. The prevention of the formation of intracellular or extracellular ice crystals and excessive dehydration of the cells is decisive for freeze preservation over long periods of time and thawing with the greatest possible survival rate. In this case, the following characteristics are to be taken into consideration from a physical viewpoint during freezing and thawing. Producing so-called vitrified water, in which any type of ice crystal formation is suppressed, through extremely high freezing speeds is known. However, this cannot be used for careful and positionally defined freezing of cell material, since the size of the biological cells of interest and heat conduction restricts the freezing speeds to values below a few ten thousands of degrees per second. Therefore, at the microscopic scale and under physiological conditions, segregation, i.e. formation of eutectic phases, which also include domains of pure ice, can be observed. To minimize the segregation, cell-specific freezing programs have provided the best results, particularly at the beginning of cooling (down to −30° C.), (see also S. P. Leibo et al. in "Cryobiol.", vol. 8, 1971, p. 447 et seq). In this temperature interval, cooling rates of a few degrees per minute have been shown to be more favorable than rapid temperature jumps. It is inferred from this that the cooling and thawing procedures should be performed with a biologically specific temperature profile over time.

As soon as temperatures at which ice formation begins have been reached, however, higher cooling rates are appropriate, since in this way the migratory growth of larger ice domains at the cost of smaller ones can be prevented. At temperatures below the range of −80° C., no further ice crystal growth occurs, so that cell storage over long periods of time is possible. The storage of the container with cell material which is suspended in a cryoliquid is typically performed in liquid nitrogen (at −196° C.). Since the sample container is closed, there is no direct contact with the liquid coolant phase. Comparable temperature sequences are used for thawing the cell material.

Cooling procedures are also known from preparation for electron microscope recordings (see D. G. Robinson et al. in "Präparationsmethodik in der Elektronenmikroskopie", Springer-Verlag, Berlin, 1985). In contrast to cryopreservation, which has the goal of maintaining the vitality of the cells, in electron microscopy, the least possible change in the molecular position of the cell components plays the decisive role. Therefore, during this preparation, particularly rapid freezing technologies are realized, which include, for example, shooting the sample into liquid or undercooled gases or spraying drops into an undercooled atmosphere and liquids. In this case, cooling rates of more than 10,000 degrees per second are achieved, which, however, due to the cell volume, the finite thermal conductivity, and the wettability of the material, represent a limiting value.

A general problem in cryopreservation is that not all types of cells can be cryopreserved in the same way. In particular, larger objects (cell groups or the like) or cells containing large numbers of vacuoles, which particularly occur in plant sample material, can be revitalized only with difficulty or not at all. The development of new microinjection and cell handling technologies, as well as new cryoprotectives, is directed toward these problems. A technology which is different from the preservation in containers described above is based on the freezing and/or thawing of the cell material to be preserved in adhered form on cooled surfaces (see, for example, T. Ohno et al in "Cryotechnol.", vol. 5, 1991, p. 273 et seq).

Cryopreservation on cooled surfaces is more difficult to handle than the suspension principle, but has been shown to have advantages in the investigation of the processes occurring during cryopreservation and in achieving higher survival rates during thawing. Cryopreservation on substrate surfaces allows the boundary conditions of the respective procedure, such as surface temperature, thermal conduction, cell or droplet size, etc., to be adjusted and detected more exactly and more variably than in the suspension of a cryomedium. This is particularly used in cryomicroscopy, with biological cells which are enclosed in the solvent drops being misted or sprayed onto frozen surfaces (see H. Plattner et al in "Freeze-etching, Techniques and Application", editor E. L. Benedetti et al, "Soc. Franc. Microsc. Electronique", Paris 1973, p. 81 et seq, and PCT/US94/01156). A disadvantage of the initially developed cryopreservation on substrate surfaces is that the position and arrangement of the cells cannot be controlled during misting or spraying and multiple drops and cell layers can even be deposited on top of one another.

An improvement of cryopreservation on substrate surfaces is described in EP 804 073. Biological cells surrounded by an enveloping solution are placed using a microdroplet jetting device in a predetermined way on substrates the temperature of which can be adjusted. The microdroplet jetting device, which can be driven like an inkjet printer, allows a highly precise and reproducible positioning of individual material samples on the cryosubstrate. Texturing the cryosubstrate with recesses applied in a matrix in order to allow specific procedures during cryopreservation and/or during thawing of the substrate is also known from EP 804 073. The recesses are thus particularly adapted for directed deposition of the cells. To produce test chips, with which the interaction of greatly differing cells in the thawed state is to be investigated, various cell types are deposited in or between the recesses. Furthermore, providing electrodes for implementing high frequency electric fields at the recesses, under whose effect an investigation of the cells in the thawed state can be performed, is known from EP 804 073.

Cryopreservation on cooled surfaces has had the disadvantage until now that, after the application onto the cryosubstrate, a sample-specific handling of single cells was only possible in the deep frozen or thawed state on the cryosubstrate. If processing in the thawed state was intended, the entire substrate had to be heated. However, for improvement of the investigation techniques and increased utilization of cryopreserved sample stocks, it is important to make the individual material samples accessible to specific handling.

SUMMARY OF THE INVENTION

The object of the invention is to provide an improved method for sample picking on cryosubstrates which particularly allows selective taking of preselected samples or sample groups from a cryosubstrate. The object of the invention is also to provide devices for implementing a method of this type.

These objects are achieved by a method and/or devices with features according to the patent claims, and/or. Advantageous embodiments and applications of the invention arise from the dependent claims.

According to the invention, predetermined, selective sample picking occurs on a cryosubstrate with multiple samples which are located on predetermined sample positions through positionally specific mechanical or thermal separation of the samples from the cryosubstrate and transfer of the released samples to a target substrate. Sample picking is hereby generally understood to mean any type of picking or taking of samples, if necessary with certain parts of the substrate.

Any device which is suitable as a carrier for samples frozen onto cooled surfaces is referred to in this case as a cryosubstrate (or: carrier substrate, substrate). It serves for sample preservation or storage. The cryosubstrate includes a carrier material for arranging the samples in linear or planar shapes with a functional surface texture described in detail below. According to a preferred embodiment, the carrier material consists of an inert material, such as plastic, ceramic, metal, or semiconductor material, which can be structured with a mechanical or chemical processing means known per se. The cryosubstrate preferably forms a rigid, planar, flat or curved body which is bonded in a way known per se with a temperature adjusting device. Alternatively, the cryosubstrate can, however, also be made of a flexible, film-like carrier material, for example plastic.

The carrier material is preferably implemented integrally with the surface texture (or: structure), but can also include a combination of the materials described in specific embodiments. This combination can, for example, be an electrically insulating base material with specific surface coatings made of, for example, metal. For the realization of the present invention, a functional surface texture (or: structure) is generally understood to mean any type of geometrical or material change of the cryosubstrate through which localized deposition regions are created, corresponding to the sample positions on the cryosubstrate, from which the respective sample or samples can be selectively removed without the entire cryosubstrate having to be heated. The sample picking according to the invention therefore preferably occurs on cryosubstrates in the deep frozen operating state.

The method according to the invention can be implemented with any type of sample desired which can be applied onto a cryosubstrate while deep frozen (e.g. at the temperature of liquid nitrogen). The samples preferably consist of biological material, such as biological cells or cell groups or cell components, if necessary each with an enveloping medium. The invention can, however, also be used with synthetic materials, such as vesicles, or with combinations of biological and synthetic materials.

The sample picking and transfer according to the invention occurs toward a target substrate, which refers to, in general, any type of device for further handling or manipulation of the sample. For example, storage, mechanical or chemical processing, or investigation of the sample occurs on the target substrate. The target substrate can thus also be a cryosubstrate of a further preservation system.

A positionally selective mechanical separation of samples from the cryosubstrate includes separation of predetermined deposition elements from the substrate with the respective samples or sample groups. The separation occurs with a suitable tool, preferably while maintaining the cryopreserved state of the samples. However, a mechanical separation in the thawed sample state can also be provided. A thermal separation occurs according to a first embodiment of the invention through a positionally specific increase of the substrate temperature in such a way that the appropriate sample is thawed and removed with a suitable tool (e.g. micropipette, picking needle), or that positionally specific deposition elements with preserved samples are thermally separated from the substrate. For thermal separation, electrical resistance heating or radiation heating (laser, microwaves, or the like) is used on the desired sample position. In an alternative form of thermal sample separation, freezing of the desired samples onto a textured tool, which produces stronger adhesion of the frozen samples than the adhesion to a sample carrier, is provided.

A subject of the invention is also a sample picking or sample handling system for picking and/or transferring samples from a cryosubstrate onto the target substrate, with a system of this type particularly including a functionally textured cryosubstrate, a separation device, and a control device. The separation device serves as a separation device and/or as the picker for the separated or released sample.

According to a particularly important aspect of the invention, a cryosubstrate is provided with a functionally textured surface which includes multiple deposition elements (e.g. deposition plates, deposition films), which are each implemented for accommodating one material sample and for selective mechanical or thermal separation of the sample, if necessary with a part of the deposition element, from the cryosubstrate. The dimensioning of the deposition elements is selected depending on the application. A deposition element can have characteristic dimensions of a magnitude from 1 $cm^2$ to 1 $mm^2$ or even less. The separation of entire sample groups from the cryosubstrate can also be provided.

The invention has the advantage that for the first time the restrictions of cryopreservation on temperature stabilized substrate surfaces are overcome and selective processing of individual samples is made possible. In this way, the effectiveness of single cell cryopreservation is significantly increased. The design of a cryosubstrate according to the invention is based on well controllable texturing methods that are known per se. The cryosubstrate can be produced as a disposable product from economical material. A further advantage concerns the ability to automate the overall system. Through the combination of sample picking with an image processing system, sample transfer from a cryosubstrate to one or more target substrates can be performed independently of the operator and automatically.

BRIEF DESCRIPTION OF THE DRAWINGS

Further advantages and characteristics of the invention are shown in the embodiments described in the following with reference to the attached drawings.

DETAILED DESCRIPTION OF THE INVENTION

The invention is described in the following with reference to the handling of samples which, for example, include one or more biological cells with an enveloping solution droplet and which are cryopreserved at the temperature of liquid nitrogen. The invention can be implemented in a corresponding way with the further sample materials described above. Restriction to a specific temperature range, or a specific temperature regime during freezing, storage, and thawing of the samples is not indicated. Details of these procedures are known per se and can be realized by those skilled in the art depending on the application.

Figure 1:
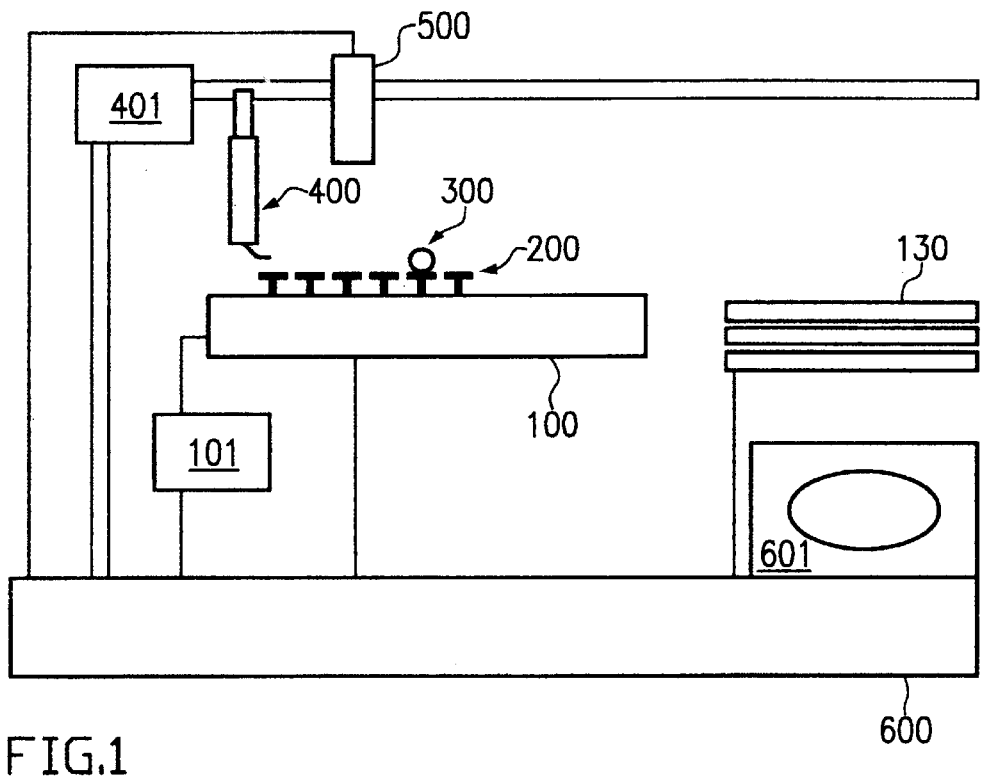
FIG. 1 shows a schematic overview of a device according to the invention for sample picking on cryosubstrates.

FIG. 1 is a schematic overview of a device according to the invention for sample picking on a cryosubstrate. The device specifically includes the cryosubstrate 100 having multiple deposition elements 200, which are each designed for cryofixed storage of a sample 300, a separation device 400, an image recording device 500, and a control system 600. The cryosubstrate 100, whose design forms are described in detail below, can have its temperature controlled with a cooling and/or heating assembly 101 in a way known per se and, if necessary, can be moved with a mechanism (not shown) in a storage device. The separation device 400 is designed for mechanical or thermal separation of samples from the cryosubstrate 100 and for transfer of the separated samples onto one or more target substrates 130. A drive unit 401 is provided for moving the separation device 400. Depending on the application, the separation device 400 can, however, also be manually operated. The provision of the drive unit 401 is a facultative feature of the invention which, however, can particularly be implemented advantageously in automated sample picking procedures on cryosubstrates. The image recording device 500 is arranged for recording an image of the surface of the cryosubstrate 100. In the control system 600, an image evaluator known per se is provided with which the surface image recorded can be evaluated in regard to the positions of the samples to be picked. The driving of the drive unit 401 can occur depending on the sample positions determined. The control unit 600 is further connected with the cooling and/or heating assembly 101, the cryosubstrate 100 (for thermal sample separation), a display 601, and possibly with the target substrates 130. In place of or in addition to the image recording device 500, an observation system, e.g. a microscope, can be provided for visual observation of the substrate surface.

According to a preferred embodiment of the invention, at least one separation device, such as a pipette head or needle head of a picking robot, can travel over the cryosubstrate and be operated at the desired sample positions. Multiple separation devices can also be positioned and actuated in a matrix like a pipette matrix with a picking robot.

Figure 2:
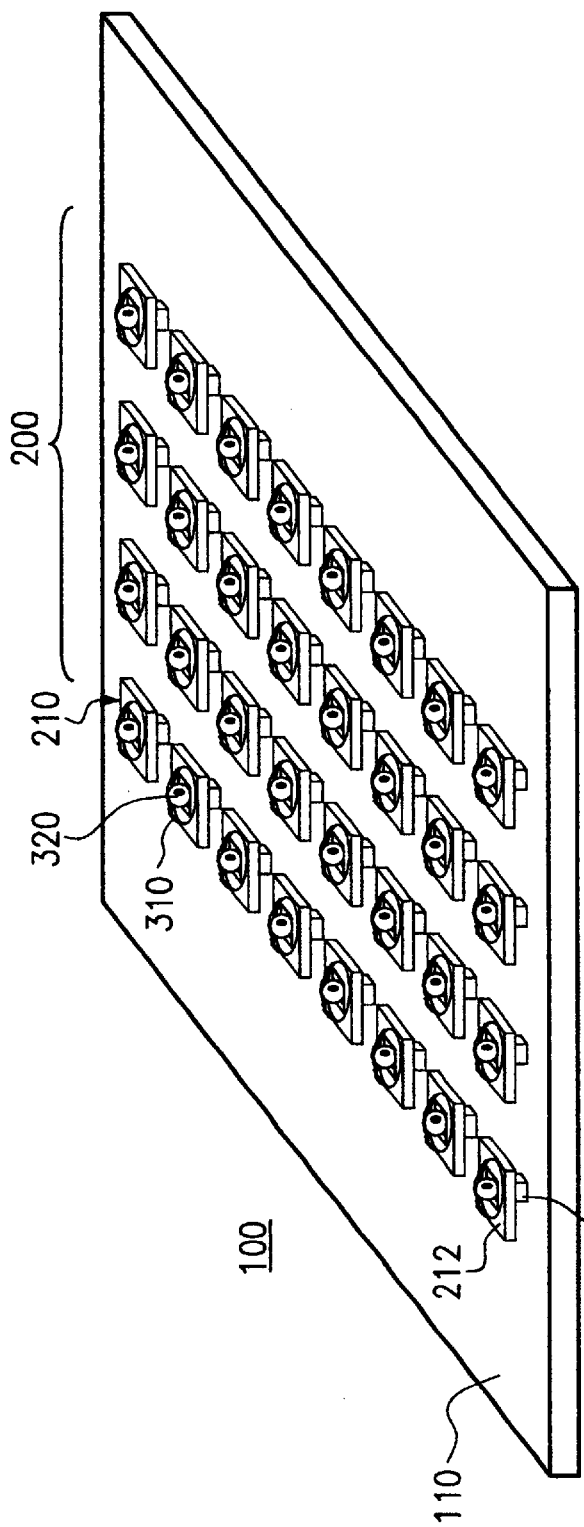
FIG. 2 shows a cryosubstrate according to the invention with mechanically separable deposition elements.

A first embodiment of the cryosubstrate 100 according to the invention is shown enlarged in a schematic perspective view in FIG. 2. The cryosubstrate 100 includes a substrate body 110 with a surface texture formed by the deposition elements 200. The substrate body 110 forms a rigid, flat body and is made of plastic (e.g. PMMA), ceramic (e.g. aluminum oxide and other sintered ceramics), metal (e.g. titanium, silver), or a semiconductor material (e.g. silicon). Ceramic and semiconductor materials have the advantage of good thermal characteristics, with high thermal conductivity particularly being sought for effective cooling.

Figure 3:
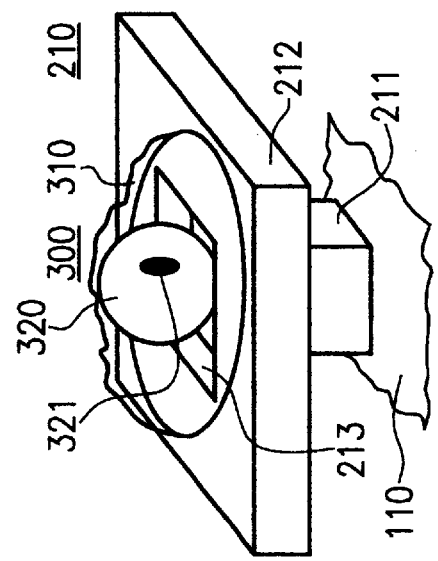
FIG. 3 shows an enlarged perspective view of a deposition element shown in FIG. 2.

The deposition elements 200 are positioned in a matrix in rows and columns. Depending on the application, altered geometries of the layout (e.g. circular, in groups, or the like) can be implemented. In the embodiment illustrated, the deposition elements 200 are formed by deposition plates 210. Details of a deposition plate 210 are illustrated in FIG. 3.

The deposition plates have the shape of a stamp or mushroom and include a carrier 211, which has a smaller cross-section, rising out from the substrate body 110, which carries a deposition lamina 212 of larger cross-section on the side away from the substrate body 210. The deposition lamina 212 has a centrally located recess 213 for accommodating the sample 300, which in the example illustrated includes a frozen enveloping solution droplet 310 with a cell 320. The reference number 321 refers to the schematically illustrated cell nucleus of the cell 320.

The design and dimensions of the deposition plate 210 are selected depending on the application, particularly in consideration of the design of the separation device (see below). The carrier 211 is implemented with a cross-section small enough that, during-the separation of the sample 300 from the cryosubstrate according to the invention, it forms a mechanical predetermined break point. In contrast, the deposition lamina 212 is implemented thicker and wider, so that during separation of the carrier 211, no damage to the deposition lamina 212 occurs.

When a forked separation device (see FIG. 4) is used, the deposition lamina preferably has the rectangular shape illustrated. However, a round shape can also be provided, particularly if a capillary separation device is used for sample picking.

The deposition elements 200 are preferably formed integrally with the substrate body 110 through a suitable structuring process. With a cryosubstrate based on silicon, the procedure is, for example, as follows. First, the substrate body 110 having a thickness of approximately 0.1 mm to 1.5 mm, e.g. based on a wafer material, is produced and provided with an $SiO_2$ film (thickness approximately 0.1 $\mu$m to 5 $\mu$m). This $SiO_2$ film is selectively etched according to the desired intervals of the deposition lamina 212 (see FIG. 2), so that the Si material of the substrate body 110 is exposed according to the row and column shape between the deposition elements 200. Underetching of the cover layer occurs in these exposed regions, so that the stamp shape illustrated is implemented.

Figure 4:
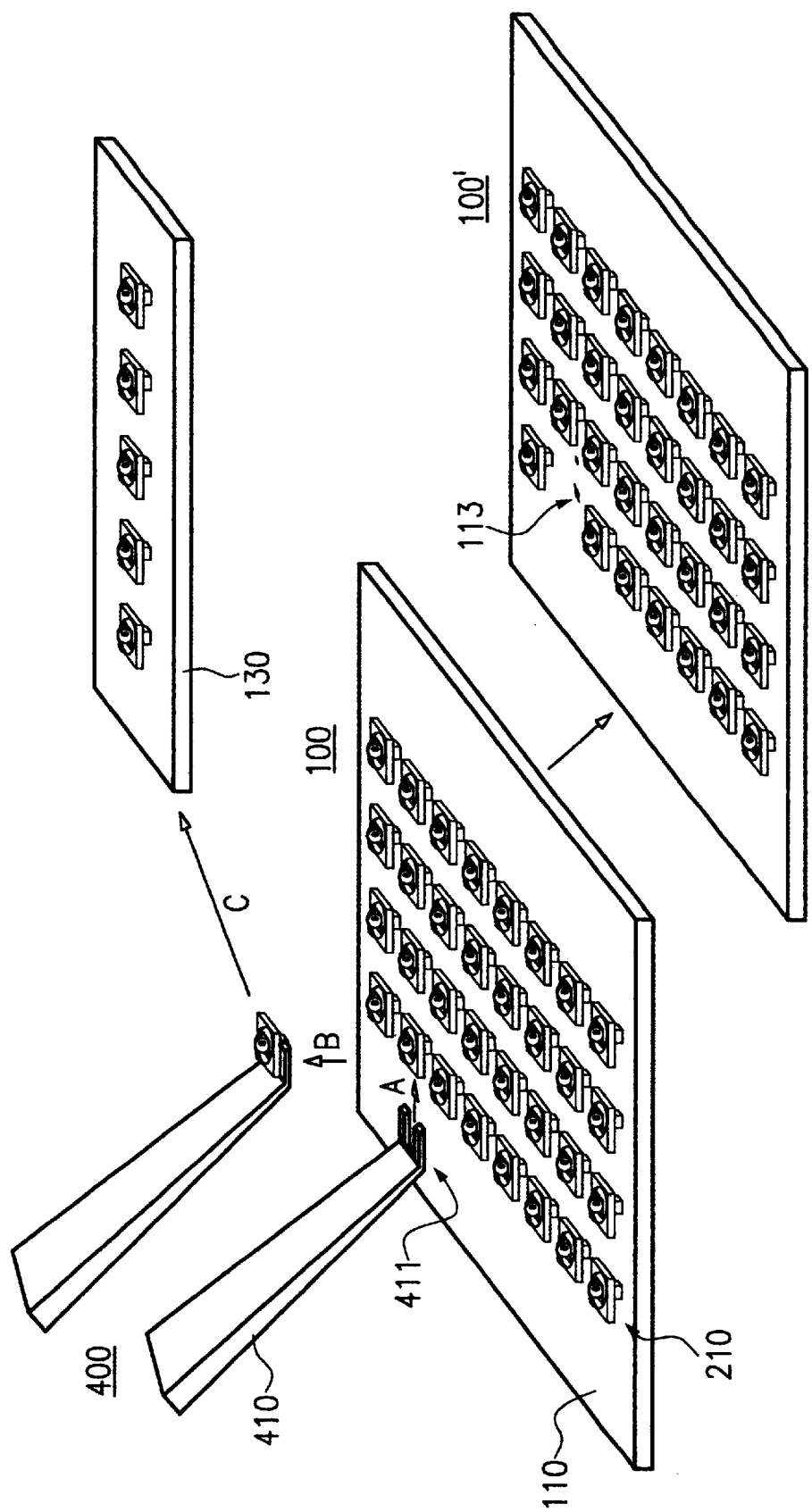
FIG. 4 shows an illustration of the transfer of individual samples from a cryosubstrate according to an embodiment of the method according to the invention.

The sample picking from cryosubstrate 100 is schematically illustrated in FIG. 4. The separation device 400 shown in a detail has a beam 410 with a forked separation tool 411 on its end pointing toward the cryosubstrate 100. The separation device 400 can be moved manually or with the drive unit 401 (see FIG. 1) in all three spatial directions in relation to the cryosubstrate 100. The beam 410 is aligned perpendicularly or at a slant to the substrate surface. The separation tool 411 extends essentially parallel to the substrate surface and includes two prong-like projections which are implemented for the purpose of engaging under one deposition plate 210 at a time and separating (breaking) it from the substrate body 110 when a specific pulling or shearing force is exercised. The separation force can, as illustrated, be generated by mechanical leverage or alternatively by exercising a vacuum on the respective deposition element, e.g. with a micropipette.

In detail, the sample picking occurs with the steps of moving the separation device 400 to the desired substrate position (arrow A), breaking or separating of the deposition plate 210 (arrow B), transfer of the samples picked (with the deposition element) to the target substrate 130 (arrow C) and storage and/or further manipulation of the sample on the target substrate 130. A gap 113 results corresponding to the sample removed in the cryosubstrate 100'.

In order that the sample 300 remains in the cryopreserved state during transfer, it can be provided that the separation device 400 itself is cooled and/or the transfer occurs with blowing of a cold stream of nitrogen. In an altered design of the separation device 400 (not shown), it has a sleeve-shaped separation tool (e.g. the tip of a micropipette) which moves over the desired deposition plate 210 from above and breaks it off with a slight shearing movement.

An alteration of the picking of samples with parts of the cryosubstrate described in FIGS. 2 to 4 is given by the following design, not shown. The functionally structured surface of the cryosubstrate has plastic film pieces positioned in a line or matrix as deposition elements, which are each glued flat like an adhesive strip onto the substrate body. The pieces of film have a size selected depending on the application, like that, for example, of the deposition plates 210 according to FIG. 2. For sample picking, a suitable stripping tool with a cutting edge or blade is used which engages under the edge of the desired film piece and pulls it off of the cryosubstrate with the sample. The film is glued onto the substrate body with a suitable adhesive. Affixing the film so it adheres without an adhesive is, however, also possible. Alternatively, the entire substrate body can also be covered with a flat film, from which individual pieces are cut out for selective sample picking, as is described with reference to FIG. 8.

Figure 5:
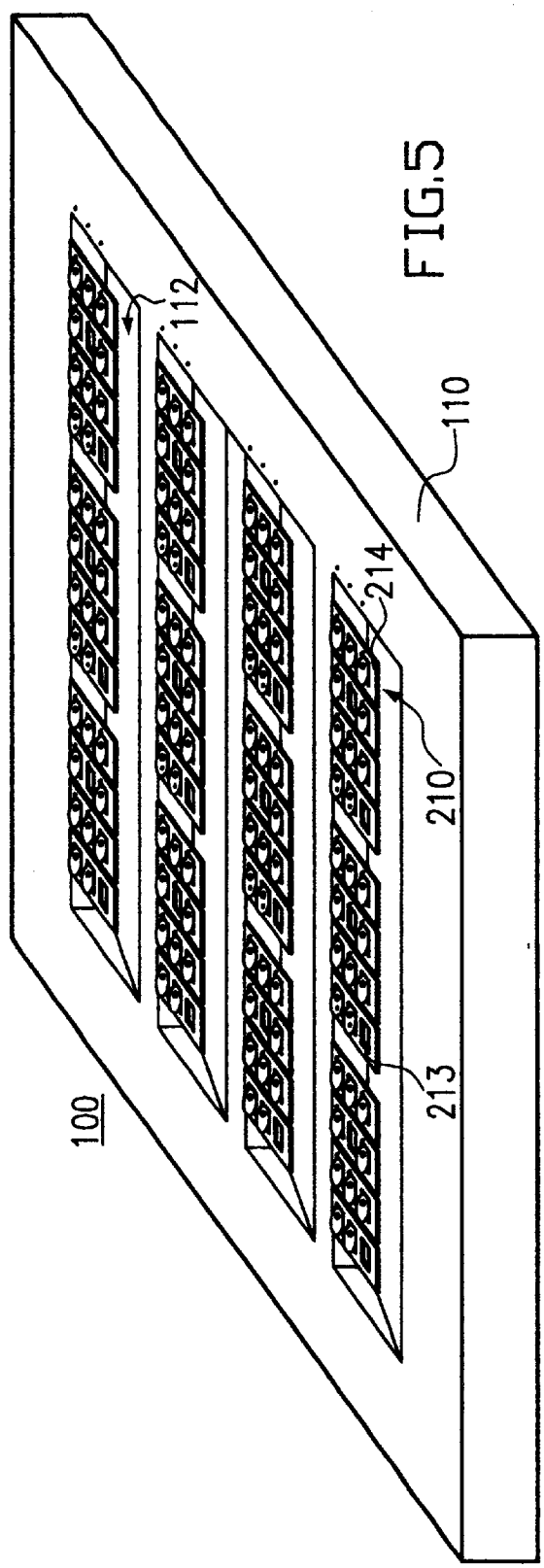
FIG. 5 shows a further cryosubstrate according to the invention with mechanically separable deposition elements.
Figure 6:
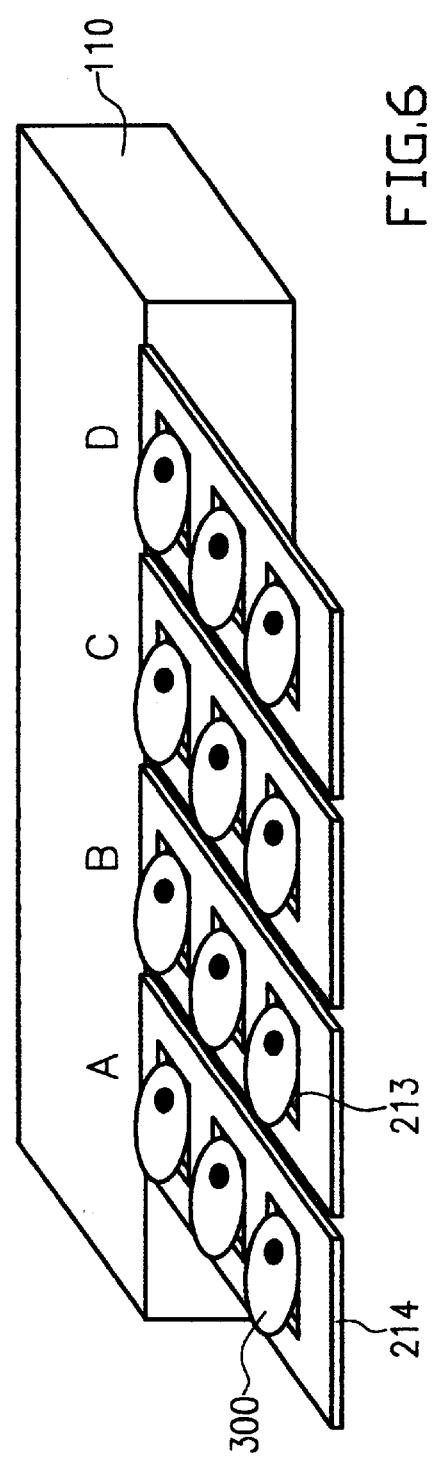
FIG. 6 shows an enlarged perspective view of four deposition elements as shown in FIG. 5.

FIG. 5 illustrates a further embodiment of a cryosubstrate 100 according to the invention having a surface-textured substrate body 110, in whose surface recesses 112 having a wedge-shaped cross-section are etched and/or undercut in rows in such a way that unsupported deposition tongues 214 are formed as the deposition plates 210. Each deposition tongue is arranged to accommodate one or (as shown) more samples 300. An enlarged illustration of the deposition tongues 214 is shown in FIG. 6. Each deposition tongue is textured with three recesses 213, in each of which one cell sample 320 is located.

The deposition tongues 214 have a predetermined break point on their ends pointing toward the substrate body 110, at which the separation using a suitable tool occurs. The separation device is again preferably equipped in this case with a forked separation tool or also with a gripping or clamping tool or a suction device for picking the deposition tongues 214.

The production of a cryosubstrate corresponding to the embodiment illustrated in FIGS. 5 and 6 using semiconductor material occurs through anisotropic etching of the recesses 112 (undercutting of the deposition tongues 214).

The letters A-D in FIG. 6 indicate a possibility of marking for the individual deposition elements of the cryosubstrate. The marking makes the orientation of the operator during observation of the cryosubstrate through a microscope and, possibly, also image evaluation in the control system 600 (see FIG. 1) easier.

Figure 7:
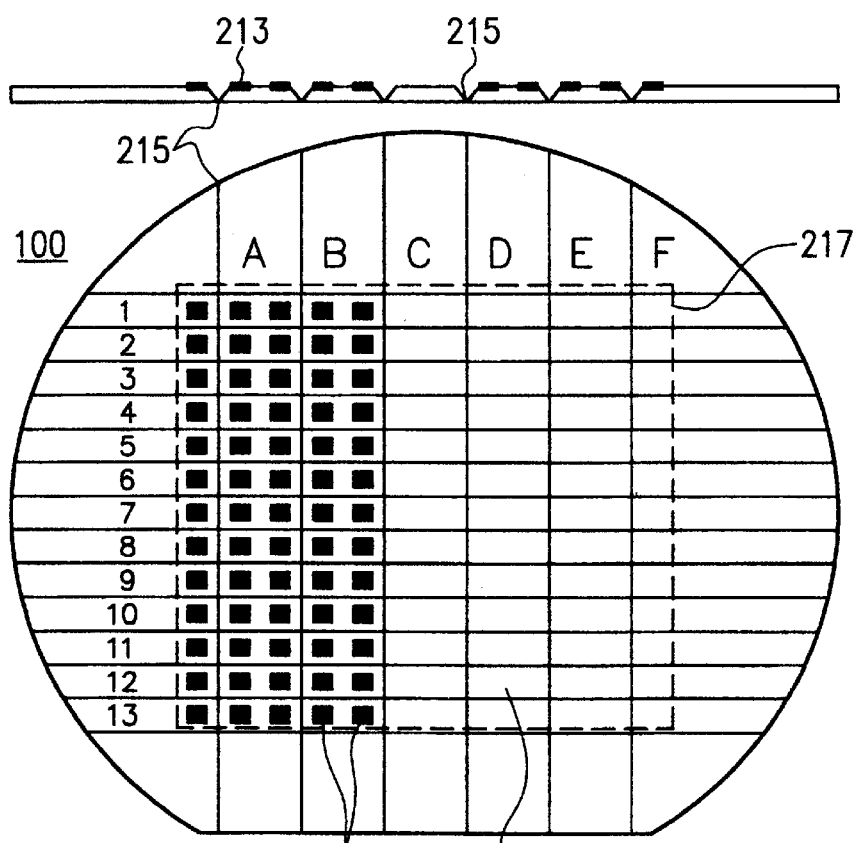
FIG. 7 shows a further cryosubstrate according to the invention which is implemented for simultaneous separation of multiple samples.

The picking in groups of one sample or multiple samples, respectively, from a cryosubstrate 100 is illustrated in FIG. 7 in a schematic side view (upper part of the image) and a horizontal projection (lower part of the image). The cryosubstrate 100, e.g. in the form of a wafer, carries a texture on its surface in the shape of linear tapers 215, which divide the substrate surface into segments 216 arranged in rows and columns. The tapers 215 form intended break points which allow selective separation of individual samples or sample groups arranged in rows or columns. The areas filled out in black schematically illustrate depressions 213 corresponding to the depressions 213 of the deposition laminas 212 and/or the deposition tongues 214 described above. Each depression 213 is again intended to accommodate one sample in the cryopreserved state.

The implementation of the tapers 215 occurs, depending on the substrate material, through a suitable texturing process, e.g. through etching, milling, or the like. The reference number 217 relates to a schematically drawn region which is used for cryopreservation on the cryosubstrate 100.

Figure 8:
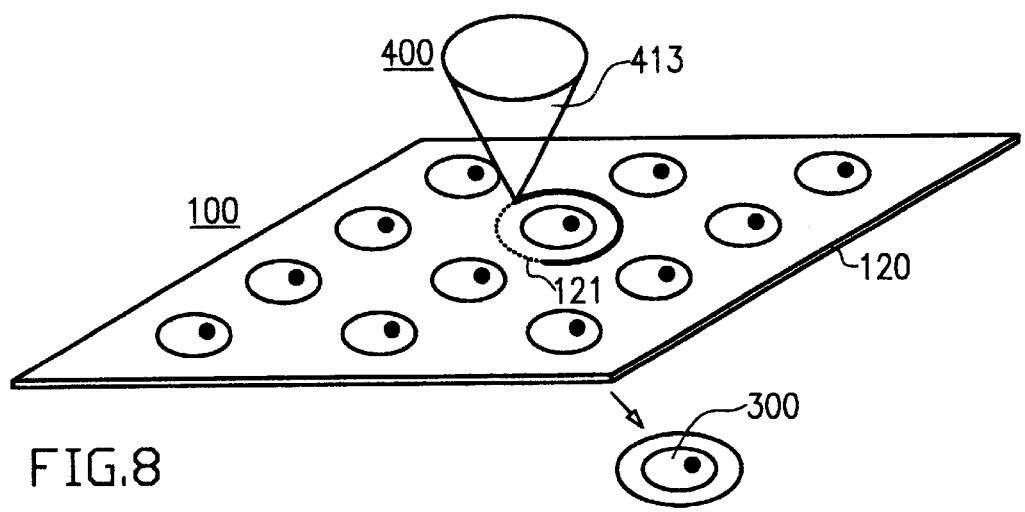
FIG. 8 shows a further cryosubstrate according to the invention in the form of a flexible film.

A further embodiment in which mechanical separation of a part of the substrate on which a sample is deposited is provided is illustrated in FIG. 8. The cryosubstrate 100 is formed by a substrate film 120. The surface texture (not shown) of the substrate film 120 includes a circular or frame-shaped separating line at each intended sample position, at which the substrate film 120 is preferably cut through and/or a grid-shaped marking network is produced by printing sample positions. In this design, for picking samples according to the invention, it is provided that the substrate film 120 be cut around the desired sample with the separation device 400 and the sample be transferred with the section of the substrate film to the target substrate. The separation device 400 is a cutting device or, as is shown in the example, an optical means in the form of a laser beam 413 focused on the substrate film 120. The laser beam allows cutting through the substrate along the cutting line 121, like a mechanical cutting device. The substrate part cut out is picked with a picker, e.g. a micropipette with a vacuum applied to it, and transferred to the target substrate.

In the following, an embodiment of the sample picking according to the invention is described with reference to the FIGS. 9 to 14, in which a thermal separation of the desired samples (possibly with parts of the substrate) occurs. In this case, various designs are provided which allow the samples to be picked in the deep frozen state or in the thawed state.

Figure 9:
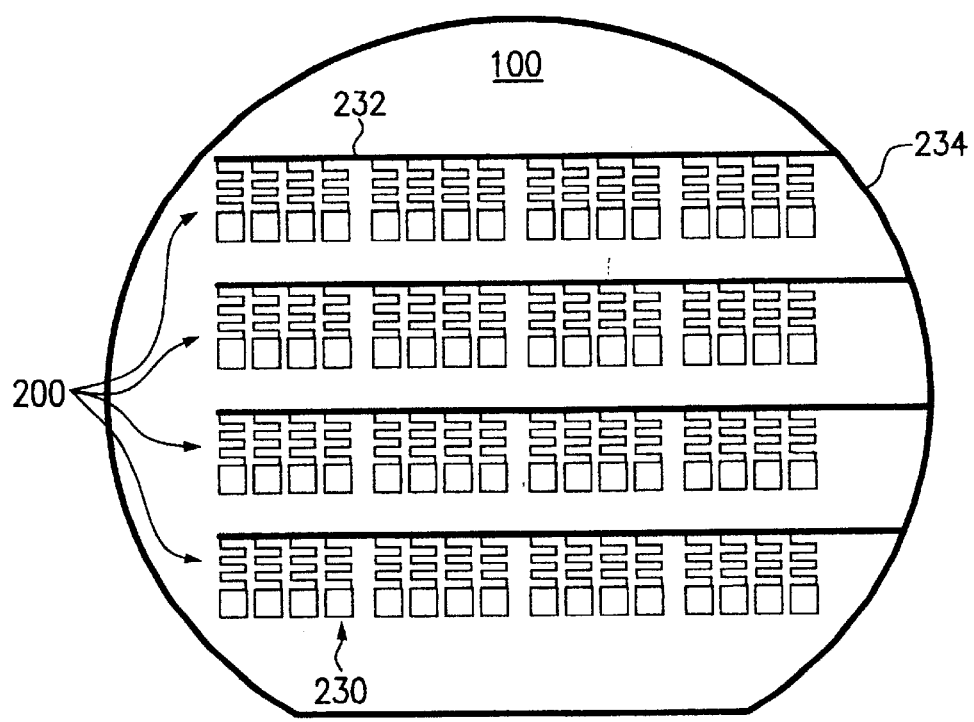
FIG. 9 shows a further cryosubstrate according to the invention which is adapted for thermal sample separation.

In the embodiment shown in FIG. 9, the cryosubstrate 100 carries deposition elements 200 in the form of multiple heating elements 230 positioned in rows and columns, which each have a heating region 231, a ground connection 232 implemented jointly for all heating elements 230, and a control connection 233. The heating region 231, the ground connection 232, and the control connection 233 are shown enlarged in FIG. 10. These components again form a functional texture on the surface of the cryosubstrate 100 in which sample deposition at specific sample positions corresponding to the location of the heating region 231 and thermal sample separation upon electrical current flow through the respective heating element 230 is provided. The substrate material is made of, for plastic or ceramic. The heating elements 230 can be formed from any suitable, preferably inert, conductive material (e.g. platinum). The ground connections 232 in rows are preferably electrically connected with one another via a ground line 234 surrounding the entire cryosubstrate 100.

Each of the heating elements 230 again has characteristic dimensions in the cm to mm range, but can also be implemented significantly smaller, down to the $\mu$m range. The respective heating region 231 is formed by a narrow, preferably meander-shaped, conductor strip, which heats up when current flows between the control connection 233 and the ground connection 232. The control connection 233 is implemented as a touchpad which can be subjected to a voltage for achieving the desire heating current through the heating region 211 applied to it by placing a movable electrode on it (see below).

Figure 11:
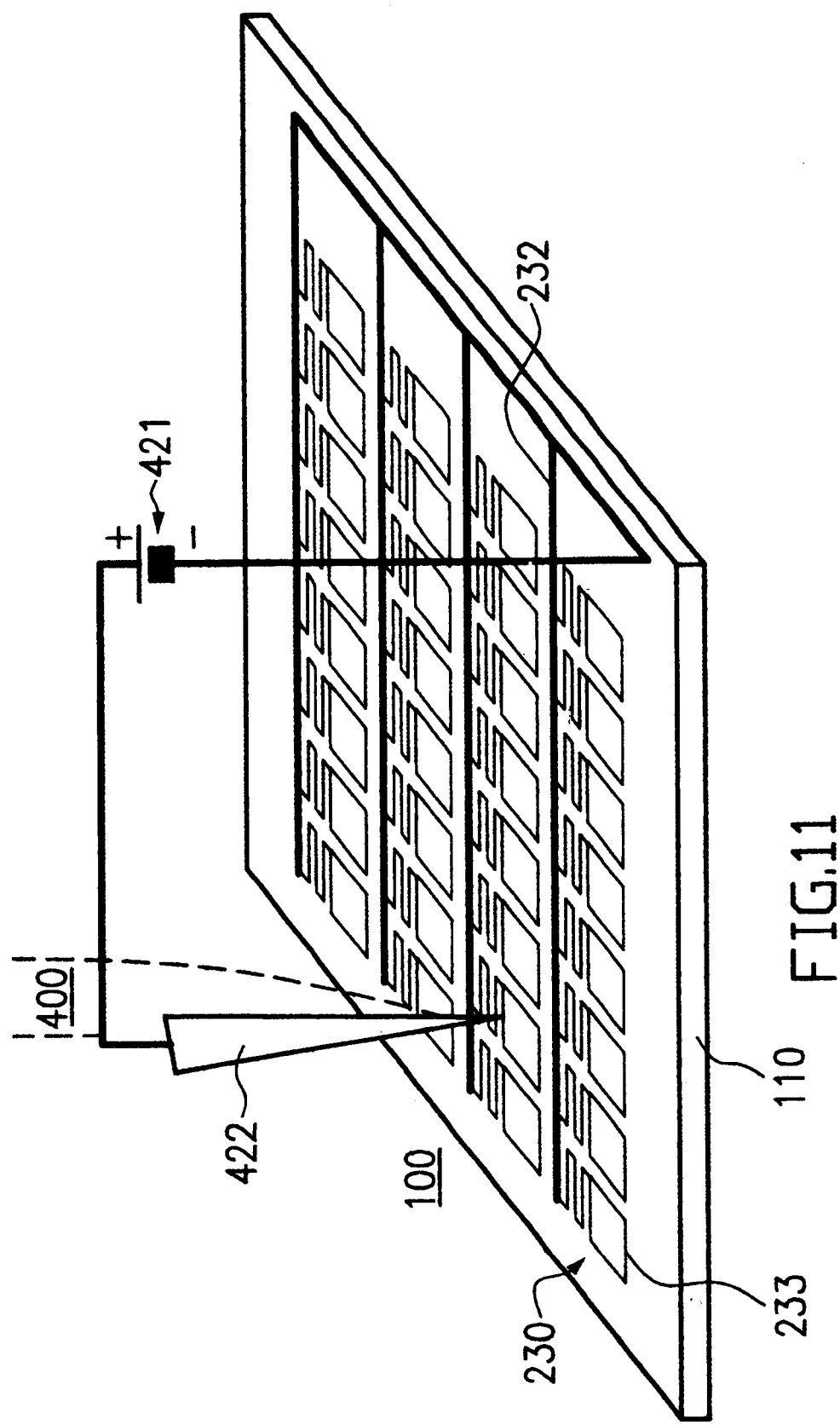
FIG. 11 shows an illustration of a further embodiment of the method according to the invention using the cryosubstrate shown in FIG. 9.

The selective thermal sample separation is also illustrated in the schematic perspective view shown in FIG. 11. FIG. 11 again shows the substrate 100 with the substrate body 110, which carries the heating elements 230 positioned in rows and columns. The ground connections 232 are all connected with the negative pole of a heating current source 421. The positive pole of the heating current source 421 is connected with a tracer electrode 422 of the separation device 420, otherwise only schematically shown with dashed lines, for positionally selective thermal release of samples from the cryosubstrate 100. The tracer electrode 422 can be moved together with the separation device 420 or separate from it in relation to the cryosubstrate 100. The placement of the tracer electrode 422 on one control connection 234 of a heating element 230 at a time provides a current flow and therefore heating of the heating region 231, so that the sample (not shown) positioned on the heating region 231, thaws partially or completely from the substrate and can be picked with the separation device 420. This device is preferably designed as a micropipette.

The tracer principle illustrated in FIG. 11 can be modified as follows. It can be provided that, in place of the single tracer tip 422, a group of tracer tips for releasing a group of samples is used according to a preselected pattern. Furthermore, a plug principle can be realized in place of the tracer principle. It is also possible to provide each row of heating elements with a joint ground connection separated from the connections of the other rows and to provide a joint control connection separated from the connections of the other columns for each heating element column. In this design, the sample release occurs in such a way that the heating current source 421 is connected by a control device with a row-column pair whose intersection point exactly corresponds to the position of the desired sample.

Figure 12:
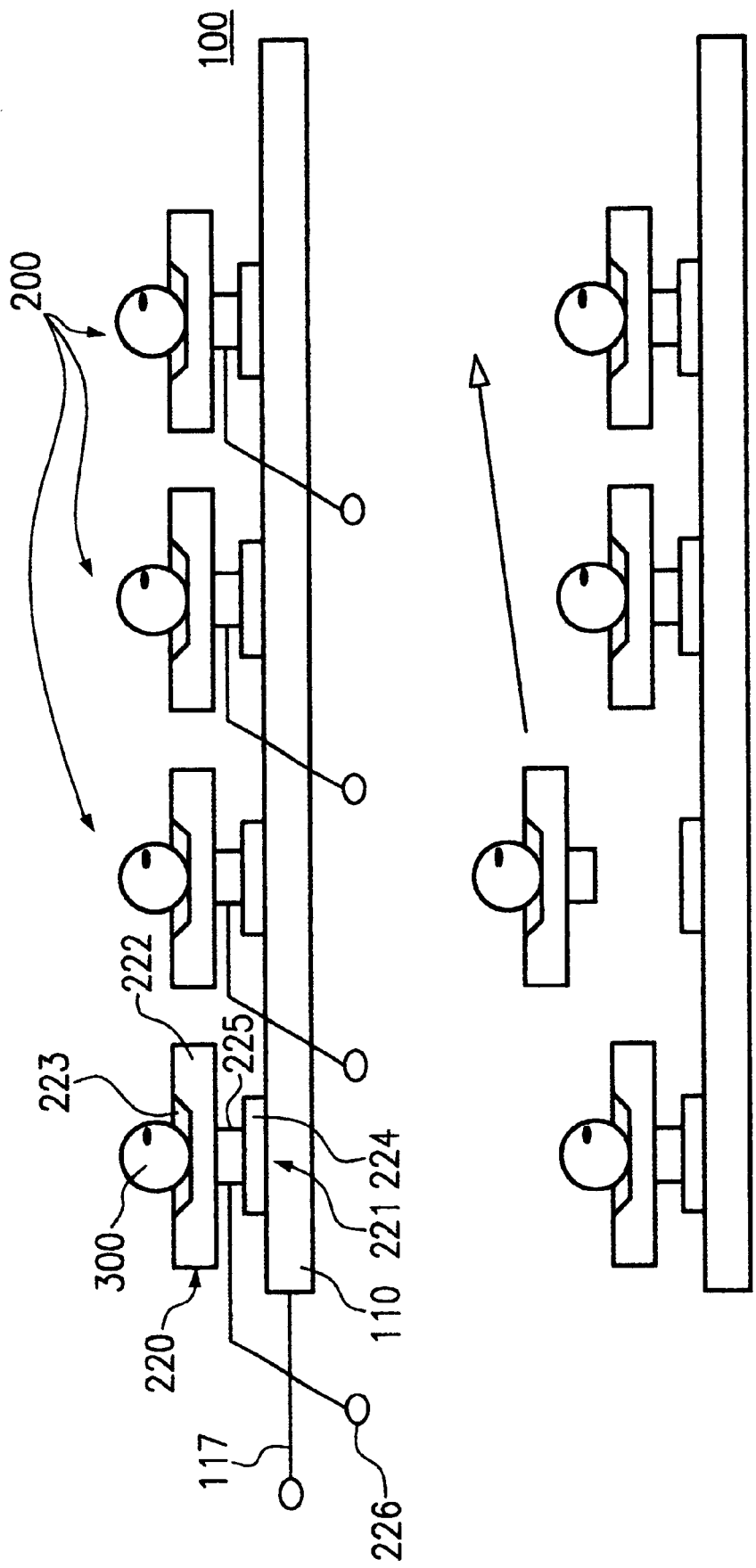
FIG. 12 shows a schematic sectional view of a further embodiment of a cryosubstrate according to the invention with thermal separation of deposition elements.

FIG. 12 shows an altered embodiment of the thermal sample picking according to the invention, in which a part of the deposition element is also separated from the cryosubstrate with each sample. The cryosubstrate 100 includes the substrate body 110 and the deposition elements 200 as a surface texture in the form of electrically detachable deposition plates 220. Each deposition plate 220 includes a carrier 221 and a deposition lamina 222. The deposition lamina 222 is provided with a recess 223 for accommodating the sample 300, as in the embodiments described above. Each carrier 221 includes a separating element 224 and a connection element 225, which is separated by the separating element 224 from the substrate body 110. The separating element 224 is made of, for example, electrically conductive components, which, upon heating due to a current flowing through them, melt or decompose or at least allow separation of the deposition lamina 222 from the substrate body 110.

The substrate body 110 is made completely or partially from metal and is provided with an electrical connection 117, which is electrically connected on the substrate side with all of the separating elements 224. Each connection element 225 is provided with its own electrical control connection 226. If a connection pair 117, 226 of a specific deposition element 220 now has a voltage applied to it, the current flow through the separating element 224 thus causes it to melt or weaken, so that the deposition element 200 affected can be picked with a suitable tool (see, for example, FIG. 4) and transported to the target substrate. This is illustrated in the lower part of FIG. 12.

The separating element 224 preferably consists of a material which changes due to the current flow (e.g. dissolves), such as a non-noble metal (aluminum or the like), a gel, etc., and has a thickness of less than 0.5 mm.

The advantage of the arrangement according to FIG. 12 is that, in spite of the thermal sample picking, the sample 300 can remain in the cryopreserved state.

Figure 13:
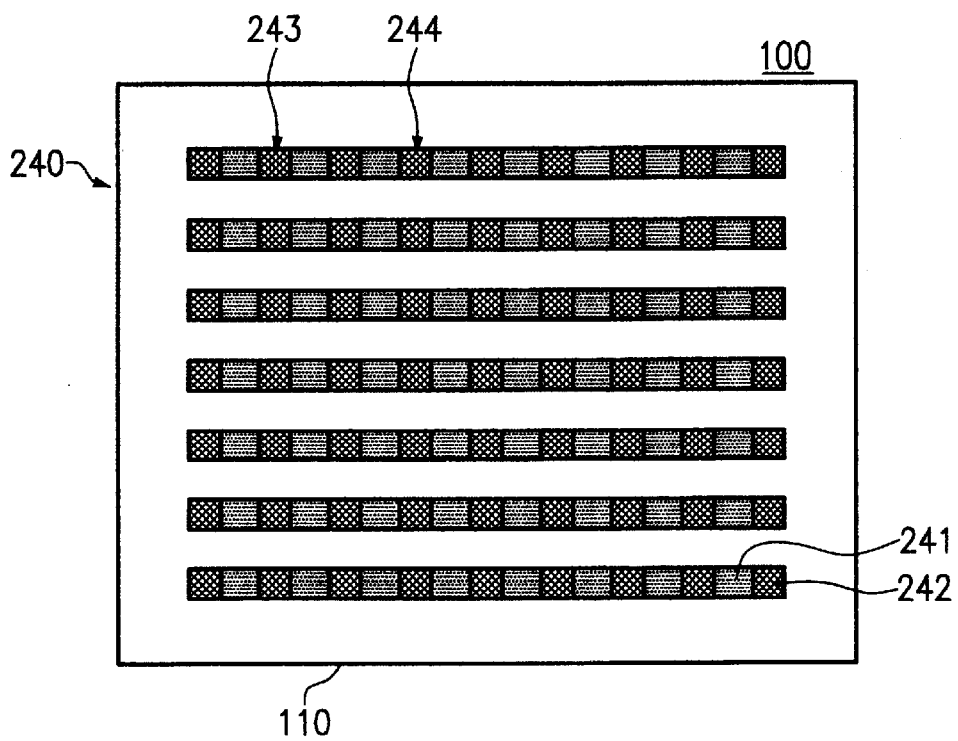
FIGS. 13, 14 show further surface textures on cryosubstrates.
Figure 14:
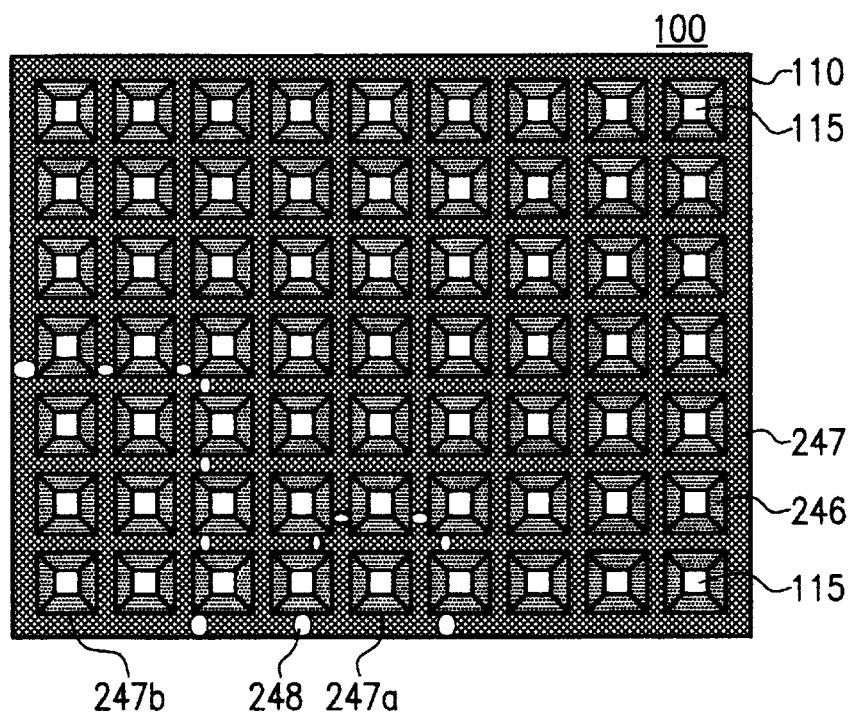

Alterations of a functional cryosubstrate with surface-integrated heating elements which are individually controllable according to the sample positions are illustrated in FIGS. 13 and 14 in a schematic top view. According to FIG. 13, the substrate body 110 of the cryosubstrate 100 carries straight electrode strips 240 which alternately enclose regions of reduced electrical conductivity 241 and regions of elevated electrical conductivity 242. The electrode strips have a characteristic width which corresponds to the typical transverse dimension of the deposition surface of the cryopreserved samples. The samples 300 are positioned in the regions 241 of reduced electrical conductivity. In contrast, the regions of elevated electrical conductivity 242 form tracer connections and/or supply points for a heating current.

Figure 10:
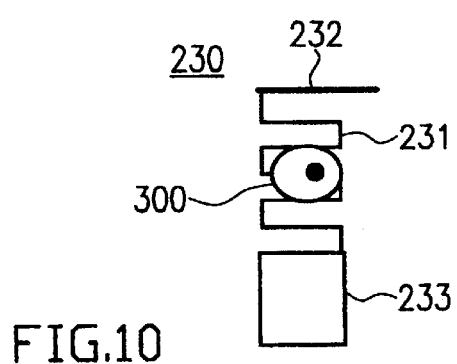
FIG. 10 shows an enlarged illustration of a heating element as shown in FIG. 9.

With two movable tracer tips analogous to the tracer electrode 422 in FIG. 10 or with a suitable line circuit, it is provided for sample picking according to the invention that two regions of elevated electrical conductivity 242 at a time have a heating voltage applied to them. The current flow between the two driven regions provides heating in the region of reduced electrical conductivity 241 between the driven regions 242, so that the samples positioned there are released. At the same time, multiple sample regions can also be included, as is illustrated by the arrows 243, 244, which show two electrical tracer electrodes which are each connected with the connections of a heating current source. Thus, the strip design shown in FIG. 13 also allows the release of sample groups positioned in rows. Sample picking then again occurs with a suitable tool, such as a micropipette or a picking needle, on whose tip the sample adheres. FIG. 14 shows an alteration of the principle shown of deposition of the samples on substrate regions of lower electrical conductivity, which are electrically connected with neighboring regions of elevated electrical conductivity, in the example of a cryosubstrate 100 having multiple openings 115 in the substrate body 110. The positions of the openings correspond to the desired sample deposition positions. The openings 115 have a smaller diameter than the characteristic cross-sectional dimensions of the samples to be deposited (e.g. for the deposition of biological cells smaller than 100 $\mu$m). The openings 115 are provided with a coating, on both sides of the substrate body 100, which forms a region of reduced electrical conductivity 246. The coatings on both substrate sides are electrically connected with one another. Otherwise, the substrate body 100 is provided. on both sides of the substrate with a coating which forms one or more regions of elevated electrical conductivity 247. The regions 247 allow driving of individual deposition positions (247*a*) or of sample groups (247*b*). For this purpose, the electrically conductive, preferably metallic coating for forming the regions 247 is cut through at the desired positions (e.g. at 248) depending on the application (introduction of slot-shaped interruptions or the like).

By applying an electrical heating voltage to the continuous coating of higher conductivity on the back of the substrate on one side and of the desired region 247 corresponding to a preselected sample, the desired heating current flows over the warming regions 246, which causes at least partial thawing of the sample and therefore its release.

Figure 15:
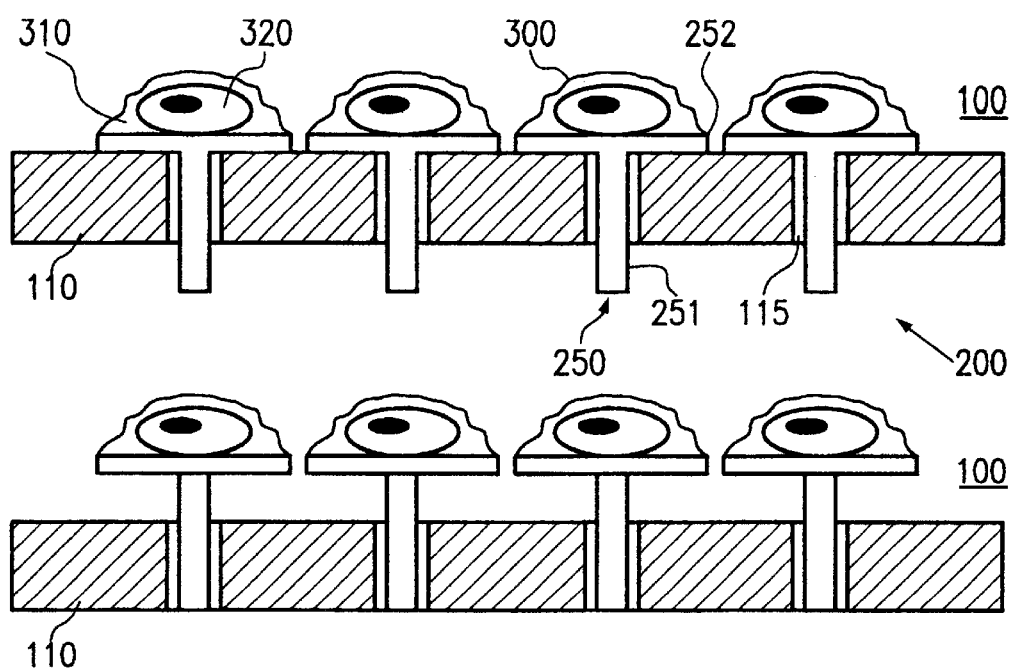
FIG. 15 shows a schematic sectional view of a cryosubstrate according to the invention with individually movable deposition elements.
Figure 16:
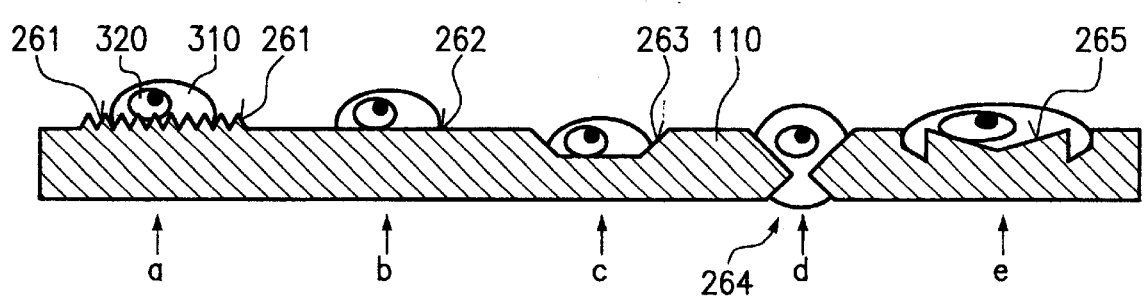
FIG. 16 shows surface textures for influencing the adhesiveness of the samples on cryosubstrates.

A further embodiment of a functionally textured cryosubstrate 100 for selective sample picking is shown enlarged in a schematic side view in FIG. 15. The substrate body 110 of the cryosubstrate has multiple openings which are positioned, for example, in a matrix in rows and columns according to the desired sample deposition. The deposition elements 200 are formed in this embodiment by movable deposition plungers 250, which are each movably located in one of the openings. Each deposition plunger 250 includes a carrier rod 251 and a deposition lamina 252, which is possibly provided with a recess (corresponding to the recess 213 shown in FIG. 2 or 3) or with a surface texture as shown in FIG. 16 (see below). The deposition laminas 252 are arranged for accommodating the cryopreserved samples 300, which, in the example shown, again include an enveloping solution droplet 310 with a biological cell 320.

In the initial state and/or in the storage state of the cryosubstrate at low temperatures, all deposition plungers 250 sit in the corresponding openings 115 in such a way that the deposition laminas 252 rest on the surface of the substrate body 110. The length of the rod element 251 is greater than the thickness of the substrate body 110, so that the rod elements 251 project out of the lower side of the substrate in the initial state.

For selective (sample-specific) sample picking or sample picking in groups, single deposition plungers 250 or groups of deposition plungers 250 are now mechanically lifted from the substrate surface from the rear side of the cryosubstrate 100. This state is illustrated in the lower part of FIG. 15 for four deposition plungers. The deposition plungers 250 pushed forward can then be lifted with a suitable separation or gripping tool, such as that described above with reference to FIG. 4, and transferred to the target substrate. At the same time, the cryopreserved state of the samples can be maintained.

It can be advantageous for the various sample picking procedures on the cryosubstrates to anchor the samples with a higher or lower retention force on the cryosubstrate. For this purpose, the substrate is textured at the sample deposition positions, so that the contact region between the substrate and sample is enlarged or modified to achieve the desired retention forces. Examples of these types of textures are shown in FIG. 16.

According to structure a, a nanotextured or microtextured roughening 261 is provided on the surface of the substrate body 110. This roughening 261 is produced, for example, with a chemical treatment or a laser treatment of the substrate and serves for better adhesion of the sample 300. According to the detail b, an extremely smooth surface is provided which, for example, is formed by a polished region 262. Inside the polished and possibly partially hydrophobic region 262, the sample 300 can be easily displace or separated from the substrate, even in the deep frozen state. This makes changing the position or picking the sample on the cryosubstrate easier. According to detail c, the sample 300 is deposited in a trough 263, which serves both for improved anchoring on the substrate and for protection against, for example, the tools during separation of neighboring samples. The texture 260 of the substrate can also include a profiled opening 264 according to detail d. The opening 264 has a smaller diameter than the biological cell 320 contained in the sample 300. Since, however, the enveloping solution droplet 310 can at least partially penetrate the opening 264 during the freezing procedure, a particularly strong anchoring of the sample in the cryopreserved state results. The detail e illustrates further substrate profiles in the form of cups or trenches, which serve to influence the droplet shape during the freezing process and/or to solidly anchor the sample to the substrate.

Figure 17:
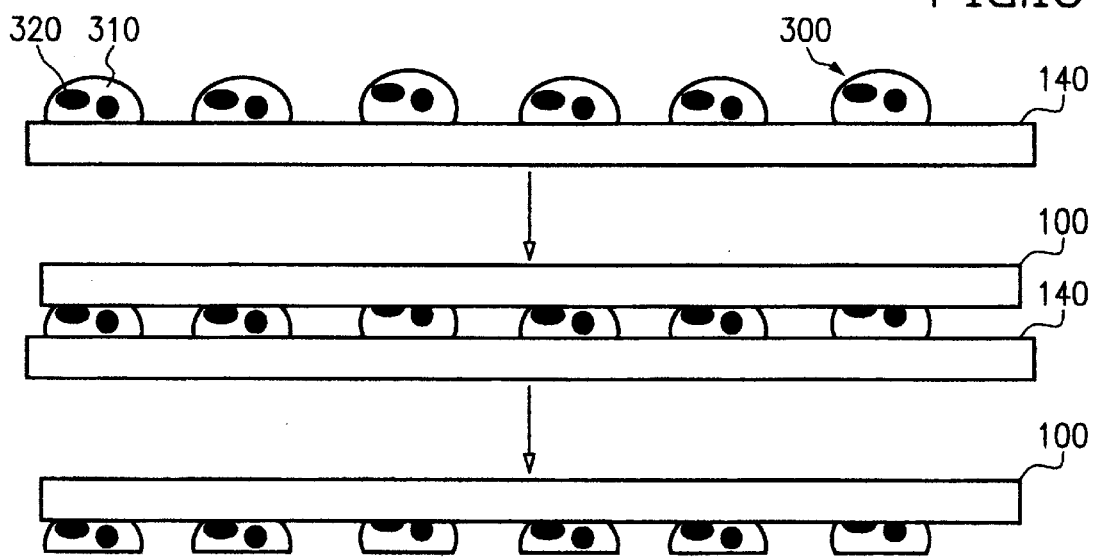
FIG. 17 shows an illustration of a further method for sample picking according to the invention.

FIG. 17 shows a further variant of sample picking according to the invention on cryosubstrates, which particularly serves for producing sample patterns on the cryosubstrate. In the uppermost image of FIG. 17, a sample carrier 140 of any desired type is shown, which carries multiple samples 300 at normal temperature (liquid state of the samples 300). Each sample 300 includes, for example, an enveloping solution droplet 310 and two cells 320. The sample pattern on the sample carrier 140 is, for example, produced with a picking robot with the aid of micropipettes.

After completion of the pattern, a deep frozen cryosubstrate 100 is placed on the samples 300 (central image in FIG. 17), so that the samples 300 freeze. The cryosubstrate 100 has textures 260 for increasing adhesion on the surface facing the samples, as was described, for example, in FIG. 16. The sample carrier 140, in contrast, has a smooth, preferably polished surface. During the freezing process, the samples 300 therefore adhere more strongly to the cryosubstrate 100 than to the sample carrier 140 and can therefore be lifted with the cryosubstrate 100 (lowermost image of FIG. 17).

The method illustrated in FIG. 17 has the advantage of a defined freezing procedure (cryoprocedure) for all of the samples. In addition, the droplets have a planar surface after adhesion on the cryosubstrate, which is particularly advantageous for microscopic observation.

The embodiments described above of the mechanical and/or thermal sample picking according to the invention through separation of single or multiple samples (possibly with parts of the substrate) from the cryosubstrate can particularly, depending on the application, be modified for specific cryosubstrate shapes (e.g. cylindrical surfaces) or for specific separation tool shapes. Furthermore, it can be provided that the sample picking according to the invention is combined with a measurement method in which the cryopreserved samples are examined on the cryosubstrate in regard to specific properties and are then automatically removed from the cryosubstrate.

A cryosubstrate according to the invention can, depending on the application, be adapted in regard to its material, shape, size, and surface design for specific measurement tasks. Thus, for NMR examinations, for example, it can be provided that the cryosubstrate is made of an inert material suitable for NMR examinations, and is tailored in size and shape to the respective available NMR measurement devices. Furthermore, a marking of cryosubstrates or of their parts, e.g. in the form of barcodes, color codes, visually detectable patterns, or electromagnetic markings (transponders) can be provided. This advantageously allows automatic detection of preselected samples on specific deposition elements and/or the detection of the specific positions from which samples are to be picked.

According to a further embodiment of a cryosubstrate according to the invention, deposition elements which are designed for positionally specific separation from the cryosubstrate can include a magnetic material. Magnetic deposition elements can easily be detected with a magnet at the end of an appropriate picking device and transferred to the respective target substrate.

The features of the invention described in the preceding description, the drawings, and the claims can be of significance both individually and in any desired combination for the implementation of the invention in its various embodiments.

What is claimed is:

1. A method of sample picking on a cryosubstrate, on which multiple cryopreserved samples are each located at preselected sample position, comprising the steps of selectively separating single samples mechanically or thermally from the cryosubstrate and transferring the samples to a target substrate.

2. A method according to claim 1, wherein, for mechanical separation of the samples, deposition elements, on each of which a sample is located, are selectively removed with a separation device from a substrate body of the cryosubstrate by exercising mechanical pulling or shear forces and each sample thus picked is transferred together with the deposition element to the target substrate.

3. A method according to claim 2, wherein the removal of the deposition elements includes breaking off of deposition plates, which are connected with the substrate body via predetermined break points, or pulling off of deposition films.

4. A method according to claim 2, wherein the removal of the deposition elements includes selective displacement of deposition plungers and picking of the displaced deposition plungers with a gripping device.

5. A method according to claim 2, wherein the removal of the deposition elements includes selective cutting out of deposition regions from a film substrate and picking of the cut out regions with a gripping device.

6. A method according to claim 1, wherein, for thermal separation of the samples, at deposition elements, on each of which a sample is located and which are formed by hearing elements, a selective, at least partial thawing of the respective sample with the heating element occurs.

7. A method according to claim 6, wherein the heating elements each have a control connection and the sample picking includes placement of a tracer electrode on the control connection for selective heating of the appropriate sample and picking of the sample with a separation device.

8. A method according to claim 1, wherein, for mechanical separation of the samples, deposition elements, on each of which a sample is located, are selectively removed with a separation device from a substrate body of the cryosubstrate by exercising a thermal decomposition and the respective sample picked is transferred together with the deposition element to the target substrate.

9. A method according to claim 1, wherein a portion of the cryosubstrate in a region of the samples remaining on the cryosubstrate remains at a cryogenic temperature during the sample picking.

10. A method according to claim 2, wherein sample groups are selectively picked.

11. A method according to claim 6, wherein sample groups are selectively picked.

12. A method according to claim 8, wherein sample groups are selectively picked.

13. A device for sample picking on cryosubstrates, which includes:
   a functionally surface-textured cryosubstrate having multiple deposition elements for cryopreserved samples, with the deposition elements being implemented for selective mechanical or thermal separation of the samples from the cryosubstrates, and
   a separation device which is implemented for separating and picking the samples from the cryosubstrates.

14. A device according to claim 13, wherein the deposition elements include deposition plates, which are each connected via a predetermined break point with a substrate body of the cryosubstrate.

15. A device according to claim 14, wherein the separation device include,des a forked separation tool, a gripping tool, a clamping tool, or a suction device.

16. A device according to claim 13, wherein the deposition elements include deposition plungers, which are displaceably positioned in a substrate body of the cryosubstrate perpendicular to its surface.

17. A device according to claim 16, wherein the separation device includes a forked separation tool, a gripping tool, a clamping tool, or a suction device.

18. A device according to claim 13, wherein the deposition elements include heating elements, which are implemented for at least partial thawing of the respective deposited sample.

19. A device according to claim 18, wherein the heating elements each have a heating region, which is connected with a ground connection and a control connection, with all ground connections of the heating elements being electrically connected with one another and the control connections being selectively electrically separated from one another and able to have a heating voltage applied to them for application to the heating elements.

20. A device according to claim 13, wherein the deposition elements include electrically removable deposition plates, in each of which a separation element is provided, which, upon application of an electrical voltage, allows separation of the sample with the deposition plate from the substrate body through melting or decomposition of the separation element.

21. A cryosubstrate which forms a carrier for multiple samples located on a surface of the cryosubstrate in a frozen state, wherein the surface has multiple deposition elements for accommodating one sample each, with each deposition element being designed for selective separation of the respective sample from the cryosubstrate.

22. A cryosubstrate according to claim 21, wherein the deposition elements include deposition plates which are connected via predetermined break points with a substrate body of the cryosubstrate.

23. A cryosubstrate according to claim 21, wherein the deposition elements include heating elements which are designed for at least partial thawing of the respective deposited sample.

24. A cryosubstrate according to claim 21, wherein the deposition elements include deposition plungers, which are as displaceable in a substrate body of the cryosubstrate perpendicular to a surface of the cryosubstrate.

25. A cryosubstrate according to claim 21, wherein film pieces are provided as the deposition elements, which can be pulled off of the substrate body in a cooled state of the cryosubstrate.

26. A cryosubstrate according to claim 21, wherein the deposition elements on the substrate surface include a surface modification for influencing the sample adhesion, said surface modification being a surface roughening, a polishing, a recess, an opening, or an anchoring trench.

27. A cryosubstrate according to claim 21, wherein the deposition elements are made at least partially from magnetic materials.

28. A cryosubstrate according to claim 21, on whose surface optical or electromagnetic markings are provided for identifying the cryosubstrate and/or individual deposition elements on the cryosubstrate.

* * * * *